(12) United States Patent
Garcia et al.

(10) Patent No.: US 11,643,376 B1
(45) Date of Patent: May 9, 2023

(54) LIQUID FLUSH TO REMOVE AND PREVENT SOLIDS ACCUMULATION IN A HEAT EXCHANGER FOR A LIQUID PHASE HYDROGENATION REACTOR

(71) Applicant: Chevron Phillips Chemical Company LP, The Woodlands, TX (US)

(72) Inventors: Israel Garcia, Kingwood, TX (US); Vincent D. McGahee, Kemah, TX (US)

(73) Assignee: Chevron Phillips Chemical Company, LP

( * ) Notice: Subject to any disclaimer, the term of this patent is extended or adjusted under 35 U.S.C. 154(b) by 0 days.

(21) Appl. No.: 17/821,372

(22) Filed: Aug. 22, 2022

(51) Int. Cl.
| | |
|---|---|
| *C07C 5/10* | (2006.01) |
| *B01J 14/00* | (2006.01) |
| *B01J 19/24* | (2006.01) |
| *B01J 19/00* | (2006.01) |
| *C07C 5/02* | (2006.01) |
| *C10G 75/00* | (2006.01) |

(52) U.S. Cl.
CPC ............... *C07C 5/10* (2013.01); *B01J 14/00* (2013.01); *B01J 19/0013* (2013.01); *B01J 19/245* (2013.01); *B01J 19/2465* (2013.01); *C07C 5/02* (2013.01); *B01J 2208/00707* (2013.01); *B01J 2219/00092* (2013.01); *B01J 2219/00103* (2013.01); *B01J 2219/00247* (2013.01); *C10G 75/00* (2013.01)

(58) Field of Classification Search
CPC .... C07C 5/10; C07C 5/02; B01J 14/00; B01J 19/0013; B01J 19/245; B01J 19/2465; B01J 2208/00707; B01J 2219/00092; B01J 2219/00103; B01J 2219/00247; C10G 75/00
See application file for complete search history.

(56) References Cited

U.S. PATENT DOCUMENTS

2019/0256443 A1* 8/2019 Snell ................... B01J 19/2465

* cited by examiner

*Primary Examiner* — Ali Z Fadhel
(74) *Attorney, Agent, or Firm* — Klemchuk PLLC (57) ABSTRACT

Removal of solids accumulations that are attached to an inlet tube sheet of a heat exchanger in a hydrogenation reactor system by injecting a flush liquid through an injection port on the heat exchanger. Injecting the flush liquid removes portions of the solids accumulations.

20 Claims, 4 Drawing Sheets

LIQUID FLUSH TO REMOVE AND PREVENT SOLIDS ACCUMULATION IN A HEAT EXCHANGER FOR A LIQUID PHASE HYDROGENATION REACTOR

FIELD OF THE DISCLOSURE

The present disclosure generally relates to hydrogenation reactors, and more particularly to the cooling loop of a liquid phase hydrogenation reactor.

BACKGROUND

Cyclohexane can be produced using a liquid phase benzene hydrogenation reactor. As the hydrogenation reaction is quite exothermic, heat must be continuously removed from the system. Heat is removed using a cooling loop, via which withdrawn reactor liquid continuously flows through a heat exchanger in which it is cooled. The cooled reactor liquid is returned to the hydrogenation reactor.

The hydrogenation reaction is a catalyzed reaction. Catalyst may be added to the hydrogenation reaction, for example, via the cooled liquid prior to reintroduction of the cooled liquid into the hydrogenation reactor. When using a homogenous catalyst for the liquid phase hydrogenation reactor, the catalyst can precipitate out of solution. The solid precipitates fall to the bottom of the hydrogenation reactor and into the cooling loop. Solid precipitates can accumulate in portions of the cooling loop, including the heat exchanger. When solid accumulations foul the heat exchanger, and cooling capacity of the heat exchanger can be reduced. As the heat exchanger fouls, the temperature of the hydrogenation reactor increases, resulting in reduced performance of the heat exchanger, and eventually a need to shut down cyclohexane production. The decrease in run life and concomitant increase in the number of turnarounds is uneconomical and detrimental to the overall cyclohexane production.

An ongoing need thus exists for a system and process that can address heat exchanger fouling during the hydrogenation of aromatic hydrocarbon(s), and/or allow for cleaning of the heat exchanger without halting production.

SUMMARY

Disclosed is a process that can include hydrogenating a feed hydrocarbon with hydrogen in a hydrogenation reactor system in a presence of a homogeneous catalyst system to form a gas phase product stream comprising a hydrogenation product; and during hydrogenating, injecting a flush liquid into the heat exchanger and against a solids accumulation on an inlet tube sheet of the heat exchanger.

Also disclosed is a hydrogenation reactor system that can include a reactor containing a liquid reaction medium comprising a feed hydrocarbon, hydrogen, a hydrogenation product, a homogeneous catalyst system, solid particulates, or combinations thereof. The reactor is configured to hydrogenate the feed hydrocarbon with hydrogen in a presence of the homogeneous catalyst system to form a gas phase product stream comprising the hydrogenation product. The hydrogenation reactor system also can include a liquid cooling loop connected to a liquid outlet of the reactor and configured to cool a withdrawn portion of the liquid reaction medium. In aspects, the liquid cooling loop can include a pump and a shell and tube heat exchanger downstream of the pump. The pump can have an inlet fluidly coupled to a liquid outlet of the reactor and can be configured to move a withdrawn portion of the liquid reaction medium through the heat exchanger. The shell and tube heat exchanger can include an inlet header fluidly coupled to an outlet of the pump and an outlet header fluidly coupled to an inlet of the reactor, an inlet tube sheet fluidly connected to a plurality of tubes, wherein the inlet tube sheet is fluidly coupled to the inlet header of the shell and tube heat exchanger, and an injection port placed on the inlet header and configured to inject a flush liquid against a solids accumulation on the inlet tube sheet of the shell and tube heat exchanger.

Other technical features may be readily apparent to one skilled in the art from the following figures, descriptions and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Herein disclosed are a hydrogenation reactor system and process that include the liquid phase hydrogenation of hydrocarbon(s). The hydrogenation reactor system and process can include liquid phase hydrogenation, optionally followed by gas phase hydrogenation. Although described with reference to the hydrogenation of benzene to produce cyclohexane, it is to be understood that the disclosure can be applicable for the hydrogenation of other feed hydrocarbons to form other hydrogenation products.

It has been found that solids accumulation in the heat exchanger of a liquid phase hydrogenation reactor system can be located on the inlet tube sheet. More particularly, the solids can accumulate on the header side of the inlet tube sheet, which is the side that receives the reaction medium from the inlet header of the heat exchanger. Over time, the accumulation can reach a size that can block inlet holes formed in the inlet tube sheet, through which reaction medium passes for cooling in the tubes of the heat exchanger. The disclosed system and process provide for increased liquid phase hydrogenation reactor run length by removing solids accumulations on the header side of the inlet tube sheet of a heat exchanger in the hydrogenation reactor system. Removing the solids helps maintain the cooling capacity of the heat exchanger, which in turn, extends the run life of the liquid phase hydrogenation reactor. Moreover, the disclosed system and process can remove solids accumulation without stopping, pausing, or halting reactor operation.

To remove solids accumulation, the disclosed process and hydrogenation reactor system inject a flush liquid into the inlet header of the heat exchanger of the hydrogenation reactor system. The liquid is injected at a velocity such that the liquid can remove solids accumulations on the header side of the inlet tube sheet of the heat exchanger. The freed solids can fall to the bottom of the inlet header or pass through the tubes of the heat exchanger and into the liquid phase hydrogenation reactor. Injection can be performed during hydrogenation without taking the hydrogenation reactor offline. Injection can also be periodic. For example, the liquid can be injected for 10, 20, 30, 40, 50, or 60 minutes every day, week, or month.

Figure 1:
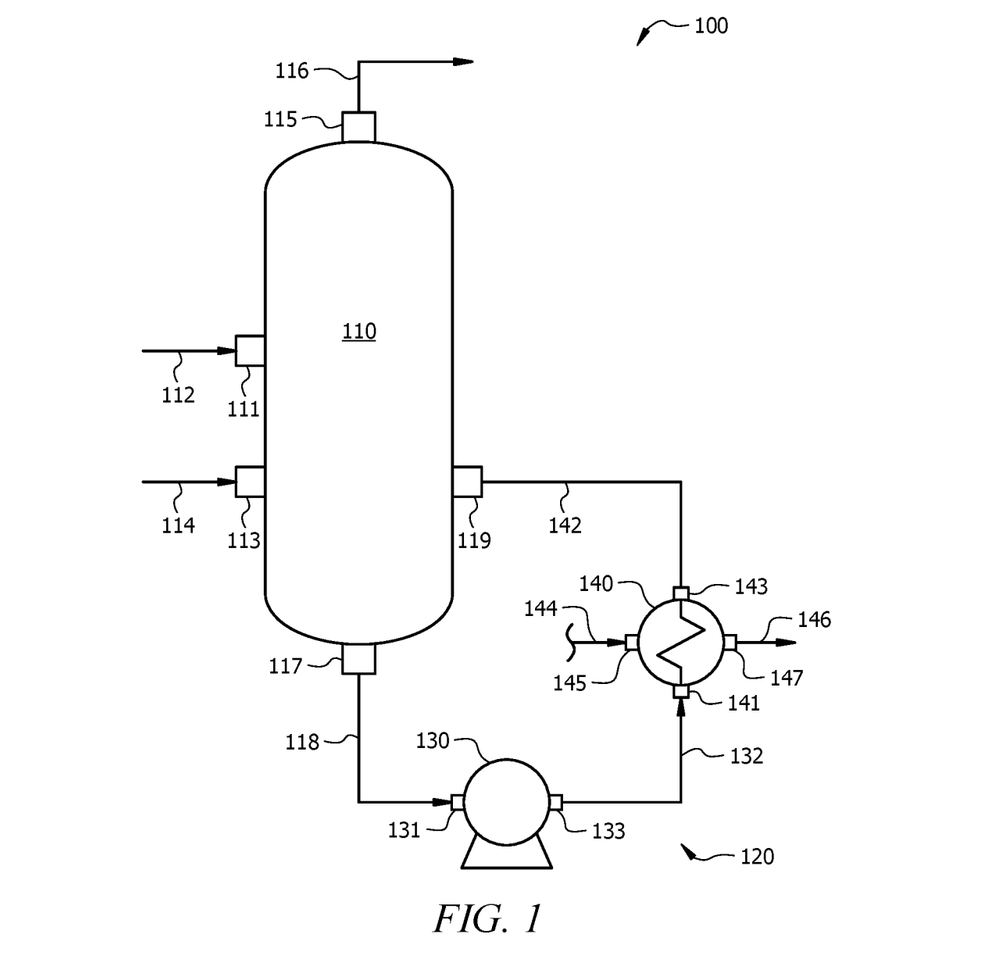
FIG. 1 illustrates a schematic diagram of a hydrogenation reactor system.

FIG. 1 illustrates a schematic diagram of a hydrogenation reactor system 100. The hydrogenation reactor system 100 can include a liquid phase hydrogenation reactor 110, and a liquid cooling loop 120 connected to a liquid outlet 117 of the liquid phase hydrogenation reactor 110 and to a liquid inlet 119 of the liquid phase hydrogenation reactor 110.

The liquid phase hydrogenation reactor 110 can have a first inlet 111, a second inlet 113, and a third inlet 119 (also referred to herein as a liquid inlet 119). The liquid phase hydrogenation reactor 110 can also have a first outlet 115 (also referred to herein as a gas phase outlet) and a second outlet 117 (also referred to herein as a liquid outlet 117).

The first inlet 111 can be fluidly coupled to a hydrocarbon feed stream 112 that contains a feed hydrocarbon. The second inlet 113 can be fluidly coupled to a hydrogen feed stream 114 that contains hydrogen. The third inlet 119 can be fluidly connected to a recycle stream 142. The hydrocarbon is introduced to the liquid phase hydrogenation reactor 110 via the first inlet 111, hydrogen can be introduced to the liquid phase hydrogenation reactor 110 via the second inlet 113, and cooled reaction medium can be introduced to the liquid phase hydrogenation reactor 110 via the third inlet 119.

In various aspects, a homogeneous catalyst system can be introduced to the liquid phase hydrogenation reactor 110 via the hydrocarbon feed stream 112, via the hydrogen feed stream 114, via the recycle stream 142, or via another via a catalyst stream that is fluidly connected to the first inlet 111, the second inlet 113, the liquid inlet 119, or another inlet of the liquid phase hydrogenation reactor 110. In some aspects, the homogeneous catalyst can be introduced into the recycle stream 142 and can flow into the liquid phase hydrogenation reactor 110 via inlet 119. The homogeneous catalyst can be added to the recycle stream 142 continuously or periodically, and the catalyst injection rate can vary depending on the application, for example between about 1 lb/hr to about 500 lb/hr (about 0.45 kg/hr to about 226.8 kg/hr).

The hydrocarbon feed stream 112 can include any feed hydrocarbon having a carbon-carbon double bond. In aspects, the hydrocarbon can include a linear olefin, a branched olefin, a cyclic olefin, or combinations thereof. In more particular aspects, the feed hydrocarbon is one or more aromatic hydrocarbons such as benzene, toluene, a xylene, styrene, or combinations thereof. The hydrocarbon feed stream 112 can be fed to the liquid phase hydrogenation reactor 110 as a liquid phase, or alternatively, as a gas phase.

Hydrogen feed stream 114 can be a gas containing hydrogen. In aspects, the hydrogen feed stream 114 can include hydrogen in an amount of greater than or equal to 90, 91, 92, 93, 94, 95, 96, 97, 98, 99, or 100 vol % based on a total volume of the hydrogen feed stream 114. In some aspects, the hydrogen feed stream 114 can include hydrogen, methane, ethane, propane, n-butane, isobutene, or combinations thereof. The flow rate of gas in hydrogen feed stream 114 can be such that hydrogen is present in the liquid phase hydrogenation reactor 110 in excess of the stoichiometric amount needed to hydrogenate the feed hydrocarbon.

Liquid reactor effluent stream 118 can include a portion of the liquid reaction medium that is withdrawn from the liquid phase hydrogenation reactor 110. The liquid reaction medium can contain hydrogenation product, unreacted feed hydrocarbon(s), homogeneous catalyst that has not converted to solid particulate, solid particulates (e.g., comprising catalyst decomposition product), or combinations thereof.

In aspects, liquid reactor effluent stream 118 can include the hydrogenation product in an amount of from about 20 vol % to about 99 vol %; alternatively, from about 50 vol % to about 99 vol %; alternatively, from about 70 vol % to about 99 vol % based on a total volume of the liquid reactor effluent stream 118.

The gas phase product stream 116 can include the hydrogenation product (e.g., cyclohexane), unreacted hydrocarbon feed (e.g., benzene), unreacted hydrogen, or combinations thereof. The gas phase product stream 116 can include hydrogenation product (e.g., cyclohexane) in a range of from about 50 vol % to about 80 vol % based on a total volume of the gas phase product stream 116. In additional aspects, the gas phase product stream 116 can include unreacted hydrogen in a range of from about 20 vol % to about 40 vol % based on a total volume of the gas phase product stream 116. In additional aspects, the gas phase product stream 116 can include methane in an amount that is greater than 0 vol % and less than or equal to about 30 vol % based on a total volume of the gas phase product stream 116.

The coolant stream 144 can include any coolant, and can be embodied as cooling water.

The warmed coolant stream 146 can include a warmed coolant. In aspects, the warmed coolant stream contains warmed coolant in the form of steam. In aspects, the steam in warmed coolant stream 146 can have a pressure in a range of from about 70 psig (482 kPag) to about 160 psig (1103 kPag); alternatively, from about 70 psig (482 kPag) to about 140 psig (965 kPag); alternatively, from about 70 psig (482 kPag) to about 125 psig (861 kPag). In aspects, the steam in warmed coolant stream 146 can have a temperature of less than or equal to about 400° F. (204° C.).

The homogeneous catalyst can include a catalyst operable to catalyze the liquid phase hydrogenation of a hydrocarbon disclosed herein to form a hydrogenation product as disclosed herein (e.g., benzene to produce cyclohexane). In aspects, the catalyst comprises a metal from Group VIII of the periodic table such as nickel, platinum, palladium, iron, or a combination thereof. In aspects, the hydrogenation catalyst can include one or more Group VIII metal species and one or more aluminum alkyl compounds. In aspects, the catalyst is soluble or colloidal in a liquid carrier such as a saturated hydrocarbon, to form the homogeneous catalyst of this disclosure. In aspects, the catalyst remains in solution or in suspension in the liquid reaction medium disclosed herein, after introduction into the liquid phase hydrogenation reactor 110 with the liquid carrier. For example, the homogeneous catalyst can include a trialkylaluminum compound, a nickel carboxylate, and a sodium carboxylate dissolved or suspended in a hydrocarbon or mixture of hydrocarbons, as described, for example, in U.S. Pat. No. 5,668,293, the disclosure of which is hereby incorporated herein for purposes not contrary to this disclosure.

The liquid cooling loop 120 is configured to cool a portion of the liquid reaction medium that is withdrawn from the liquid phase hydrogenation reactor 110 via the liquid outlet 117, and to return the cooled liquid reaction medium to the liquid phase hydrogenation reactor 110 via the liquid inlet 119. The liquid cooling loop 120 can include a liquid reactor effluent stream 118, a pump 130, a pumped stream 132, a heat exchanger 140, a recycle stream 142, a coolant stream 144, and a heated coolant stream 146.

The liquid reactor effluent stream 118 containing withdrawn liquid reaction medium can be connected to the liquid outlet 117 of the liquid phase hydrogenation reactor 110 and to an inlet 131 of the pump 130. The pumped stream 132 containing the withdrawn liquid reaction medium can be connected to the outlet 133 of the pump 130 and to an inlet 141 of the heat exchanger 140. The recycle stream 142 containing cooled liquid reaction medium can be connected to the outlet 143 of the heat exchanger 140 and to the inlet 119 of the liquid phase hydrogenation reactor 110.

The liquid phase hydrogenation reactor 110 can contain a liquid reaction medium comprising the unreacted feed hydrocarbon, hydrogenation product, hydrogen, a homogeneous catalyst system, solid particulates, or combinations thereof. The liquid phase hydrogenation reactor 110 is configured to hydrogenate the feed hydrocarbon (e.g., an aromatic hydrocarbon such as benzene) with hydrogen in a presence of the homogeneous catalyst system to form a gas phase product stream 116 comprising a hydrogenation product (e.g., a saturated hydrocarbon such as cyclohexane). In aspects, the temperature of the liquid reaction medium in the liquid phase hydrogenation reactor 110 can be in a range of from about 125° C. to about 275° C.; alternatively, from about 170° C. to about 230° C.; alternatively, from about 100° C. to about 200° C.; alternatively, from about 100° C. to about 250° C. In some aspects, the temperature is below a cracking temperature for olefins that may be present in the liquid reaction medium and received from the hydrocarbon feed stream 112 (e.g., a temperature less than about 250° C.), to prevent hydrocracking of a hydrocarbon feed. In aspects, the pressure of the liquid reaction medium in the liquid phase hydrogenation reactor 110 can be sufficient to maintain a liquid phase in the liquid phase hydrogenation reactor 110, and may be in the range of from about 5 atm to about 100 atm (0.5 MPa to 10 MPa); alternatively, from about 20 atm to about 30 atm (2 MPa to 3 MPa); alternatively, from about 15 atm to about 30 atm (1.5 MPa to 3 MPa).

Hydrogenation reaction takes place in the liquid phase hydrogenation reactor 110 such that the hydrogenation product in gas phase flows from the liquid phase hydrogenation reactor 110 in gas phase product stream 116 and liquid reaction medium flows from the liquid phase hydrogenation reactor 110 via liquid reactor effluent stream 118.

Liquid phase effluent can be withdrawn from liquid phase hydrogenation reactor 110 via liquid outlet 117 and flows in liquid reactor effluent stream 118 to the pump 130. Pump 130 is configured to withdraw a portion of the liquid reaction medium from the liquid phase hydrogenation reactor 110 and to pump the withdrawn liquid reaction medium through the heat exchanger 140 and back into the liquid phase hydrogenation reactor 110 via the recycle stream 142. The temperature of the withdrawn liquid reaction medium is reduced in the heat exchanger 140 via heat exchange with a heat exchange medium (e.g., coolant such as cooling water). In aspects, the heat exchanger 140 is configured to reduce the temperature of the withdrawn liquid reaction medium by about 5° F. to about 20° F. (2.7° C. to 11.1° C.). Cooled reaction medium can flow from the outlet 143 of the heat exchanger 140 into the recycle stream 142, for return to the liquid phase hydrogenation reactor 110.

Figure 2A:
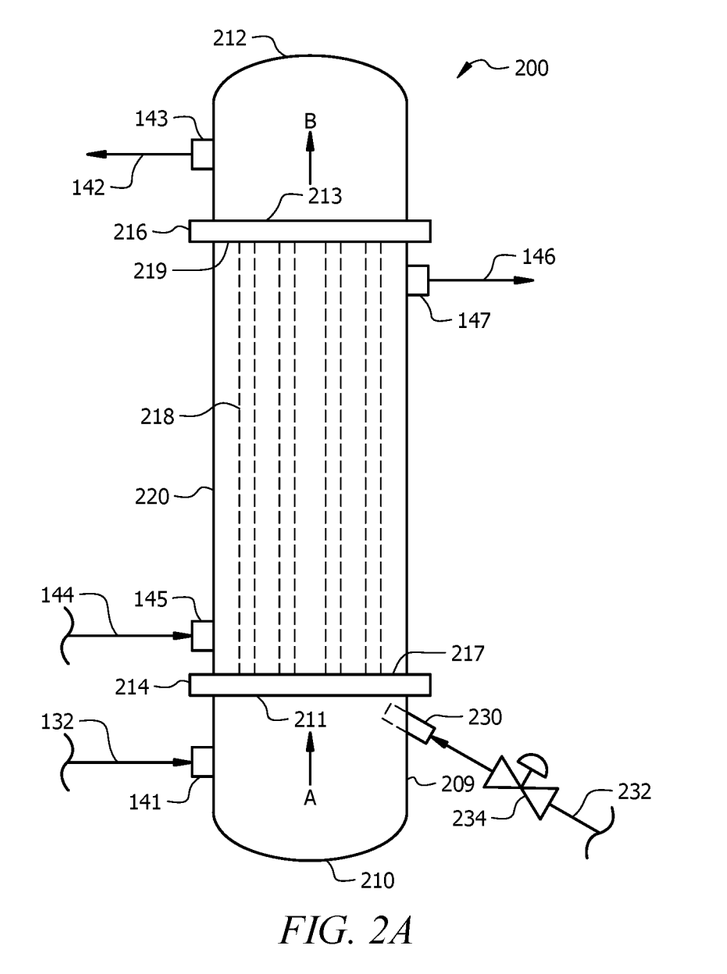
FIG. 2A illustrates a side elevational view of an embodiment of the heat exchanger of the hydrogenation reactor system.

FIG. 2A illustrates a side elevational view of an embodiment of the heat exchanger 140 of the hydrogenation reactor system 100, embodied as a shell and tube heat exchanger 200.

The shell and tube heat exchanger 200 can have an inlet header 210, an outlet header 212, a shell 220 positioned between the inlet header 210 and the outlet header 212, an inlet tube sheet 214 positioned between the inlet header 210 and shell 220, an outlet tube sheet 216 positioned between the outlet header 212 and the shell 220, and a plurality of tubes 218 (shown as dashed lines, collectively referred to as a tube bank) contained within the shell 220. Each of the plurality of tubes 218 has an end connected to a tube side 217 of the inlet tube sheet 214 and an opposite end connected to a tube side 219 of the outlet tube sheet 216. The inlet 141 for the liquid reaction medium can be seen connected to the inlet header 210, and the outlet 143 for the cooled liquid reaction medium can be seen connected to the outlet header 212. The inlet 145 for the coolant can be seen connected to the shell 220, and the outlet 147 for the warmed coolant can be seen connected to the shell 220. The inlet tube sheet 214 can be fluidly coupled to the inlet 141 of the shell and tube heat exchanger 200.

The shell and tube heat exchanger 200 also can include one or more injection ports (illustrated as injection port 230 in FIG. 2A) placed on the inlet header 210 and configured to inject a flush liquid against a solids accumulation on the inlet tube sheet 214 of the shell and tube heat exchanger 200. The shell and tube heat exchanger 200 can additionally include an injection conduit 232 connected to the injection port 230, and a control valve 234 contained in the injection conduit 232 and configured to actuate between an open position and a closed position so as to allow or disallow a flow of the flush liquid into the injection port 230 and into the outlet header 212.

In aspects, any injection port described herein can include a nozzle. At least a portion of the nozzle extends inside the inlet header 210 so as to direct a pressurized stream of the flush liquid into the liquid reaction medium in the inlet header 210 so as to contact solids accumulation(s) with the stream of flush liquid.

In aspects, the flush liquid can be any liquid that is inert to or is a component in the liquid reaction medium. For example, the flush liquid can be a mixture of hydrocarbons, such as a mixture containing a hydrocarbon that is the hydrogenation product. In aspects, the flush liquid can be sourced from hydrogenation reactor system 100, such as a being a portion of the liquid reaction medium withdrawn from the liquid phase hydrogenation reactor 110, that is pumped into the injection conduit 232 by an injection pump. In these aspects, the solid particulates contained in the liquid reaction medium can carry a greater momentum than the liquid, for removing solids accumulations. In alternative aspects, the flush liquid ca be sourced from other parts of the hydrogenation reactor system 100, or for example, from a liquid recovery of the hydrogenation product as is illustrated and described for hydrogenation reactor system 300 in FIG. 3. In any of the aspects described herein, the flush liquid can be a mixture comprising the hydrogenation product (e.g., saturated hydrocarbon such as cyclohexene); alternatively, in any of the aspects described herein, the flush liquid can contain the hydrogenation product in an amount that is greater than 99, 99.9, 99.99, 99.999 wt % based on a total weight of the flush liquid in injection conduit 232.

The shell and tube heat exchanger 200 can be operated in a vertical orientation as illustrated in FIG. 2A, where the inlet header 210 is the bottom of the shell and tube heat exchanger 200 and the outlet header 212 is the top of the shell and tube heat exchanger 200. It is contemplated that the shell and tube heat exchanger 200 can be operated in other orientations, such as a horizontal orientation where the inlet header 210 is on a side of the shell and tube heat exchanger 200 and the outlet header 212 is on an opposite side of the shell and tube heat exchanger 200.

The liquid reaction medium is received from the pump 130 via stream 132 and into the shell and tube heat exchanger 200 via the inlet 141. The liquid reaction medium enters the inlet header 210 of the shell and tube heat exchanger 200 and is directed upward in the direction of arrow A into the tubes 218 via the inlet tube sheet 214.

While passing through the tubes 218, heat from the liquid reaction medium transfers through the walls of the tubes 218 and into the coolant that flows through the shell 220 of the shell and tube heat exchanger 200. Coolant flows into the shell 220 via the coolant inlet 145, around the tubes 218 while contacting the outer surface of the tubes, and out of the shell 220 via the coolant outlet 147. Coolant warms as it travels from the coolant inlet 145 to the coolant outlet 147 by absorbing heat from the liquid reaction medium flowing in the tubes 218.

The cooled liquid reaction medium flows out of the tubes 218 via passages or holes formed in the outlet tube sheet 216, and into the outlet header 212 in the direction of arrow B. The cooled liquid reaction medium flows out of the shell and tube heat exchanger 200 via the outlet 143, and recycles back to the liquid phase hydrogenation reactor 110 via recycle stream 142.

Solid particulates that result from catalyst decomposition can be contained in the liquid reaction medium and can contact the header side 211 of the inlet tube sheet 214 as the liquid reaction medium flows through passages or holes formed in the inlet tube sheet 214 and into the tubes 218. Over time, some of the solid particulates can adhere to portion(s) of the header side 211 of the inlet tube sheet 214, and additional solid particulates can accumulate into one or more solids accumulations on the header side 211 of the inlet tube sheet 214. The solids accumulations can reduce the cooling capacity of the shell and tube heat exchanger 200. For example, the solids accumulations can at least partially block the passages or holes formed in the inlet tube sheet 214 through which the liquid reaction medium passes into the tubes 218, which reduces flow of liquid reaction medium through the shell and tube heat exchanger 200.

To remove solids accumulations, and/or to help prevent solids accumulations from growing to a size that inhibits heat exchange performance, a flush liquid can be injected into the inlet header 210 via the injection port 230. A control valve 234 in the injection conduit 232 can be actuated from a closed position to an open position. While the control valve 234 is in the open position, the flush liquid flows through the injection conduit 232 and the injection port 230 and inside the inlet header 210. The injection pressure of the flush liquid in the injection conduit 232 can provide motive force to push the flush liquid through the liquid reaction medium flowing in the inlet header 210.

Figure 3:
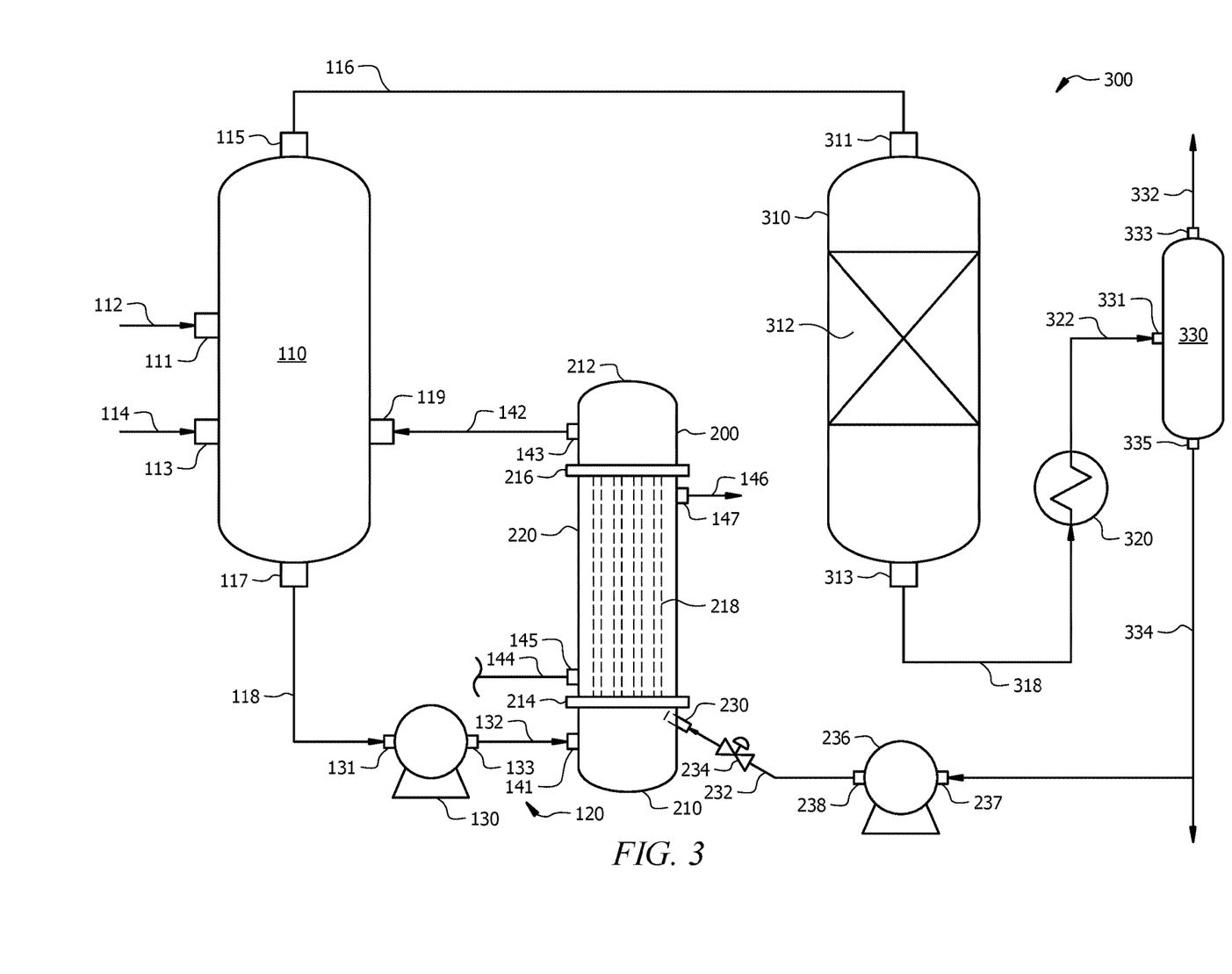
FIG. 3 illustrates a schematic diagram of another embodiment of a hydrogenation reactor system.

In aspects, an injection pressure of the flush liquid in the injection conduit 232 can be greater than the pressure of the liquid reaction medium that flows through the heat exchanger 200. In such aspects, an injection pump can be placed in the injection conduit 232 upstream of the control valve 234 (an injection pump is illustrated in FIG. 3), and the injection pressure can be provided by the injection pump.

Figure 2B:
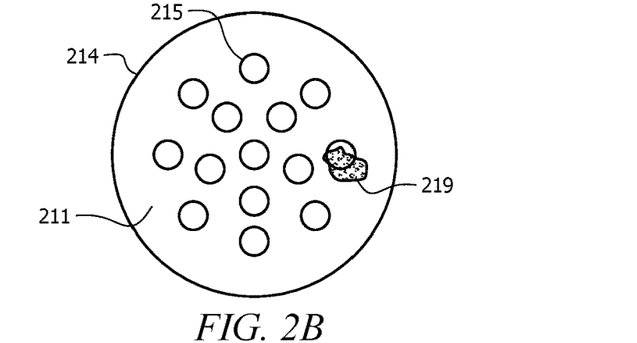
FIG. 2B illustrates a side elevational view of an inlet tube sheet for the heat exchanger in FIG. 2A.

FIG. 2B illustrates a side elevational view of the inlet tube sheet 214 for the heat exchanger 200 in FIG. 2A. The view in FIG. 2B is of the header side 211 of the inlet tube sheet 214. The inlet tube sheet 214 generally can have a disc shape. Passages or holes 215 are formed in the inlet tube sheet 214, and each passage or hole 215 extends from the header side 211 to the tube side 217 (sides 211 and 217 are labeled in FIG. 2A). An exemplary solids accumulation 219 is shown in FIG. 2B attached to a portion of the header side 211 of the inlet tube sheet 214. The pattern of the passages or holes 215 in FIG. 2B is exemplary only, and other patterns can be used, as well as any number of passages or holes 215. Additionally, any cross-sectional shape of the passages or holes 215 can be used—circular cross-sectional shapes are depicted in FIG. 2B. Each passage or hole 215 generally corresponds as an inlet or entry into a single tube of the plurality of tubes 218.

While in FIGS. 2A and 2B the entire header side 211 functions as the inlet for the liquid reaction medium, it is contemplated that other heat exchanger configurations can apply, such as for the half of the header side 211 to function as the inlet for the liquid reaction medium and half of the header side 211 to function as the outlet for the liquid reaction medium. In these aspects, the header 210 may have inlet 141 positioned on one side and outlet 143 positioned on another side, while header 212 is a recirculation header that receives liquid reaction medium from one zone of the tube bank and directs the liquid reaction medium through another zone of the tube bank, flowing out of the shell and tube heat exchanger 200 via the outlet 143 which is located on the header 210.

In aspects, the configuration of holes 215 formed in the inlet tube sheet 214 in FIG. 2B can be the same for the outlet tube sheet 216; alternatively, the inlet tube sheet 214 and the outlet tube sheet 216 can have different configurations for holes, depending on the configuration of the tube bank.

Figure 2C:
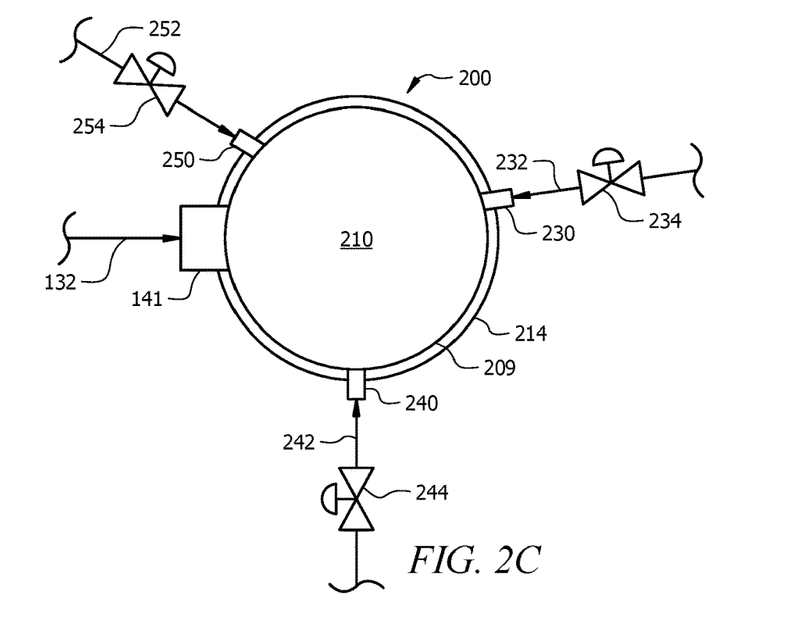
FIG. 2C illustrates a bottom view of the heat exchanger in FIG. 2A.

FIG. 2C illustrates a bottom view of the shell and tube heat exchanger 200 in FIG. 2A, having three injection ports 230, 240, and 250. The injection ports 230, 240, 250 are equally spaced around the circumference of the inlet header 210; although, alternative spacings can be used to achieve the removal of solids accumulations from the inlet tube sheet 214. Injection port 230 is connected to injection conduit 232, which has control valve 234 located therein. Injection port 240 is connected to injection conduit 242, which has control valve 244 located therein. Injection port 250 is connected to injection conduit 252, which has control valve 254 located therein.

Each of the control valves 234, 244, and 254 can be connected to a control system that is configured to actuate the control valves 234, 244, and 254 between an open position and a closed position. An open position allows flush liquid to flow through conduits 232, 242, and 252, and a closed position disallows flush liquid to flow through conduits 232, 242, and 252.

During injection periods when flush liquid is injected into the inlet header 210, the control valves 234, 244, and 254 can be actuated from a closed position to an open position at the same time, such that flush liquid flows through conduits 232, 242, and 252 at the same time; alternatively, the control valves 234, 244, and 254 can be actuated from a closed position to an open position in any combination of actuations, such as actuation of control valve 234 on and off followed by actuation of control valve 244 on and off followed by actuation of control valve 254 on and off.

While three injection ports 230, 240, and 250 are illustrated in FIG. 2C, alternative aspects contemplate that more or fewer injection ports can be utilized.

Figure 2D:
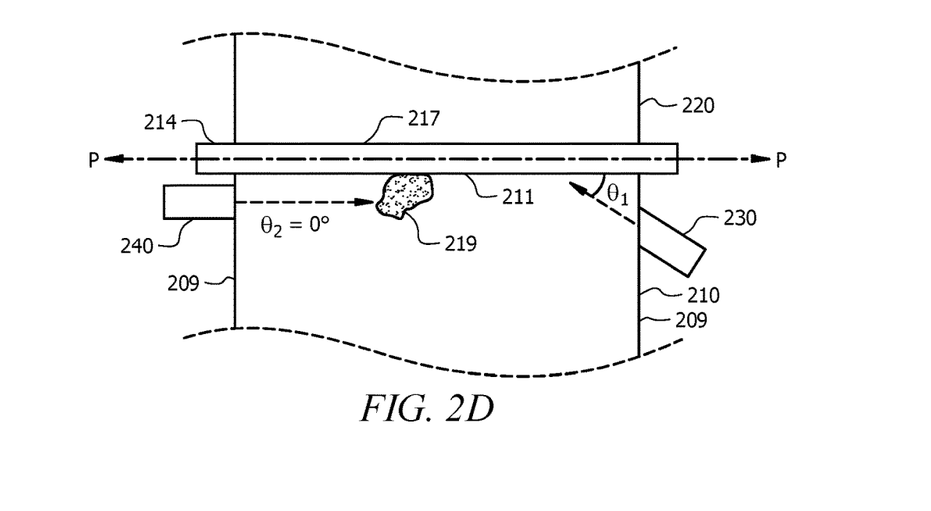
FIG. 2D illustrates an isolated side view of injection ports on the heat exchanger of FIG. 2A.

FIG. 2D illustrates an isolated side view of injection ports 230 and 240 on the shell and tube heat exchanger 200 of FIG. 2A. The inlet tube sheet 214 can be seen positioned between the shell 220 and the inlet header 210 such that the header side 211 is connected to the inlet header 210 of the shell and tube heat exchanger 200 and the tube side 217 is connected to the shell 220 of the shell and tube heat exchanger 200. The tube side 217 can be connected to an end of each tube in the plurality of tubes 218; additionally or alternatively, an end of each tube can be placed in a passage or opening of the inlet tube sheet 214.

FIG. 2D illustrates exemplary non-limiting orientations that any injection port within the disclosure may have. The orientations are generally described relative to a plane P of the inlet tube sheet 214, where the plane P is parallel to the longitudinal axis of the inlet tube sheet 214.

Injection port 230 is connected to the side 209 of the inlet header 210 such that an angle of injection θ1 relative to the plane P of the inlet tube sheet 214 is in a range of from 0° to 90°; alternatively, greater than 0° and less than 90°. Injecting flush liquid at injection angle θ1 causes the flush liquid to contact the header side 211 of the inlet tube sheet 214 and against any solids accumulation in the trajectory of the flush liquid. Injection port 240 is connected to the side 209 of the inlet header 210 such that an angle of injection θ2 relative to the plane P of the inlet tube sheet 214 is 0°, i.e., the trajectory of flush liquid is parallel to the plane P of the inlet tube sheet 214 (e.g., and perpendicular to the longitudinal axis of the inlet tube sheet 214). Injecting flush liquid at injection angle θ2 causes the flush liquid to contact any solids accumulations that is in the fluid trajectory with a lateral force in a direction that is parallel to the header side 211 of the inlet tube sheet 214.

FIG. 2D illustrates that both injection ports 230 and 240 are connected to the side 209 of the inlet header 210, spaced apart along the circumference of the side 209 of the inlet header 210. In aspects, the shell and tube heat exchanger 200 can have multiple injection ports in any combination of orientations such as those illustrated in FIG. 2D, so as to contact solids accumulations from various fluid trajectories on the header side 211 of the inlet tube sheet 214.

In aspects, a distance between an injection port (e.g., injection port 230 or 240) and the header side 211 of the inlet tube sheet 214 can be in a range of from about 1 cm to about 15 cm.

FIG. 3 illustrates a schematic diagram of another embodiment of a hydrogenation reactor system 300. The hydrogenation reactor system 300 includes the liquid phase hydrogenation reactor 110 and liquid cooling loop 120 from the hydrogenation reactor system 100 of FIG. 1, with the heat exchanger 140 embodied as shell and tube heat exchanger 200 in FIG. 2A. The connection and function of liquid phase hydrogenation reactor 110 and liquid cooling loop 120 are the same as described for the hydrogenation reactor system 100 in FIG. 1, as such, the description is not reproduced here.

The hydrogenation reactor system 300 additionally includes a gas phase reactor 310 configured to receive the gas phase product stream 116 and configured to hydrogenate unreacted feed hydrocarbon (e.g., aromatic hydrocarbon such as benzene) received from the gas phase product stream 116 to form a reaction effluent stream 318 containing the hydrogenation product. The hydrogenation reactor system 300 can further include a condenser 320 configured to cool the reaction effluent stream 318 to form a cooled effluent stream 322. The hydrogenation reactor system 300 can also include a separator 330 configured to separate the cooled effluent stream 322 into a gas stream 332 and a liquid stream 334.

An inlet 311 of the gas phase reactor 310 is fluidly coupled to the outlet 115 of the liquid phase hydrogenation reactor 110 via the gas phase product stream 116. An outlet 313 of the gas phase reactor 310 is fluidly coupled to the condenser 320 via reaction effluent stream 318. An inlet 331 of the separator 330 is fluidly connected to the condenser 320 via cooled effluent stream 322. The gas stream 332 is fluidly connected to a first outlet 333 of the separator 330, and the liquid stream 334 is fluidly connected to a second outlet 335 of the separator 330.

Any of the injection conduits connected to the inlet header 210 of the shell and tube heat exchanger 200 can be fluidly coupled to the liquid stream 334. In FIG. 3, injection conduit 232 is fluidly coupled to the liquid stream 334 such that at least a portion of the liquid in liquid stream flows into injection conduit 232 to be used as a flush liquid for the shell and tube heat exchanger 200.

The hydrogenation reactor system 300 in FIG. 3 also illustrates an injection pump 236 located in the injection conduit 232. The injection pump 236 has an inlet 237 fluidly coupled to the liquid stream 334 and an outlet 238 fluidly coupled to the control valve 234. In aspects having multiple injection ports with an injection conduit connected to each port, each injection conduit can contain an injection pump that is coupled to the liquid stream 334; alternatively, each injection conduit can be fluidly coupled to a single injection pump, such as injection pump 236. In aspects, a portion of the liquid hydrogenation product in stream 334 can flow to a storage tank that is fluidly coupled to both the liquid stream 334 and to the injection conduit 232, to provide a source of flush liquid for use during injection periods.

In operation of the hydrogenation reactor system 300, the first hydrogenation product in gas phase product stream 116 flows to the gas phase reactor 310. The gas phase reactor 310 can be embodied as one or more vessels, where each vessel contains at least one fixed bed 312 of heterogeneous hydrogenation catalyst.

The heterogeneous hydrogenation catalyst can be a solid nickel-based hydrogenation catalyst, for example, an oxidized nickel-based catalyst that is deposited on a solid support such as alumina or silica based support. In aspects of the hydrogenation reactor system 300 where benzene is the feed hydrocarbon, the use of a nickel-based catalyst can reduce the risk of pentane, hexane, or methylcyclopentane formation from the benzene that may be present in the gas phase product stream 116. In aspects, the heterogeneous catalyst in the fixed catalyst bed 312 can contain nickel in a range of 10 wt % to 50 wt % based on a total weight of the catalyst. An example of the heterogenous catalyst suitable for the fixed catalyst bed 312 is described in U.S. Pat. No. 5,668,293, the disclosure of which is hereby incorporated herein for purposes not contrary to this disclosure.

The first hydrogenation product received from the gas phase product stream 116 flows into a top of the gas phase reactor 310 and through the fixed catalyst bed 312 where unreacted feed hydrocarbon (e.g., benzene) that was not hydrogenated in liquid phase hydrogenation reactor 110 can hydrogenate with unreacted hydrogen in the presence of the heterogeneous catalyst as the unreacted feed hydrocarbon passes through the fixed catalyst bed 312, forming additional hydrogenation product such that the reaction effluent stream 318 contains less unreacted feed hydrocarbon and more hydrogenation product than the gas phase product stream 116 (e.g., more cyclohexane and less benzene that gas phase product stream 116).

The reaction effluent stream 318 can include the gas phase reactor product from the gas phase reactor 310. The gas phase reactor product can include the hydrogenation product (e.g., cyclohexane), unreacted hydrocarbon feed (e.g., benzene), unreacted residual hydrogen (hydrogen that is not reacted in either of reactors 110 and 310), or combinations thereof. The reaction effluent stream 318 can include hydrogenation product (e.g., cyclohexane) in an amount of greater than or equal to about 97, 98, or 99 vol % based on a total volume of the reaction effluent stream 318. In aspects, the reaction effluent stream 318 can be free of unreacted feed hydrocarbon, indicating complete or almost complete conversion in the hydrogenation reactor system 300. Free of unreacted feed hydrocarbon can refer to an amount of unreacted feed hydrocarbon in reaction effluent stream 318 that is less than 1, 0.1, 0.01, or 0.001 vol % based on a total volume of the reaction effluent stream 318.

The gas phase reactor product can be withdrawn from the outlet 313 of the gas phase reactor 310 via reaction effluent stream 318, and can flow to the condenser 320 for cooling. The condenser 320 can be operated to condense some or most (e.g., greater than 50, 60, 70, 80, 90, 91, 92, 93, 94, 95, 96, 97, 98, or 99 wt %) of the hydrogenation product to liquid phase. Liquid hydrogenation product and unreacted residual hydrogen gas can flow from the condenser 320 in a cooled effluent stream 322 to the separator 330. In aspects, the cooled effluent stream 322 is a two-phase stream containing hydrogenation product in liquid phase and hydrogen in gas phase. The liquid hydrogenation product separates from the hydrogen gas in the separator 330. Liquid hydrogenation product flows in liquid stream 334 from the separator 330, and hydrogen gas flows in gas stream 332 from the separator 330.

In aspects, the liquid stream 334 can contain the hydrogenation product in a range of from about 98 wt % to about 99.9 wt % based on a total weight of the liquid stream 334. In aspects, the liquid stream 334 can be free of hydrogen and unreacted feed hydrocarbon, indicating pure or almost pure hydrogenation product in the liquid stream 334. Free of hydrogen and unreacted feed hydrocarbon can refer to an amount of hydrogen and unreacted feed hydrocarbon in liquid stream 334 that is less than 2 wt % based on a total weight of the liquid stream 334.

In aspects, the gas stream 332 can contain unreacted residual hydrogen in an amount that is greater than 45 vol %; alternatively, in a range of from about 45 vol % to about 95 vol %; alternatively, in a range of from about 48 vol % to about 95 vol %, based on a total volume of the gas stream 332. In aspects, the hydrogen in gas stream 332 can be recycled to the liquid phase hydrogenation reactor 110.

In some aspects, the techniques described herein relate to a process to prevent fouling accumulation in a heat exchanger 140/200 of a liquid phase hydrogenation reactor 110. The process can include hydrogenating a feed hydrocarbon with hydrogen in a liquid phase hydrogenation reactor 110 of a hydrogenation reactor system 100 or 300 in a presence of a homogeneous catalyst system to form a gas phase product stream 116 that includes a hydrogenation product (e.g., a saturated hydrocarbon). The process can also include, during hydrogenating, injecting a flush liquid into the heat exchanger 200 of the hydrogenation reactor system 100 or 300 and against a solids accumulation 219 on an inlet tube sheet 214 of the heat exchanger 200. The process can include removing at least a portion of the solids accumulation 219 from the inlet tube sheet 214 by use of the flush liquid that flows through at least one injection port 230 located on the heat exchanger 200 at a location that is upstream of the inlet tube sheet 214 (e.g., on the inlet header 210) with respect to a direction of flow of liquid reaction medium through the shell and tube heat exchanger 200. The orientation of the injection port 230 can be any orientation described herein, and the injection port 230 can be present in combination with other injection ports as described herein. In aspects, the step of injecting can be performed intermittently. In further aspects, the process can also include controlling a flow of the flush liquid through a control valve 234 located in an injection conduit 232 that is fluidly connected to the injection port 230.

In yet further aspects, the process can also include introducing the feed hydrocarbon, hydrogen, and the homogeneous catalyst system into the liquid phase hydrogenation reactor 110, removing the gas phase product stream 116 from the liquid phase hydrogenation reactor 110, removing a portion of a liquid reaction medium including a catalyst decomposition product from the liquid phase hydrogenation reactor 110, cooling the liquid reaction medium in the heat exchanger 140 (e.g., shell and tube heat exchanger 200) to from a cooled reaction medium, and introducing the cooled reaction medium to the liquid phase hydrogenation reactor 110.

In yet further aspects, the process can include hydrogenating the gas phase product stream 116 in a presence of a heterogeneous catalyst system in the gas phase reactor 310 to form a reaction effluent stream 318, cooling the reaction effluent stream 318 to form a cooled effluent stream 322 that includes a liquid phase of the saturated hydrocarbon and unreacted hydrogen; and separating the cooled effluent stream into a liquid stream including the liquid phase of the saturated hydrocarbon and a gas stream including the hydrogen.

ADDITIONAL DESCRIPTION

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the detailed description of the present disclosure. The disclosures of all patents, patent applications, and publications cited herein are hereby incorporated by reference.

Aspects of processes and systems have been described. The following are non-limiting, specific aspects in accordance with the present disclosure:

In Aspect 1, the techniques described herein relate to a process including: hydrogenating a feed hydrocarbon with hydrogen in liquid phase hydrogenation reactor of a hydrogenation reactor system in a presence of a homogeneous catalyst system to form a gas phase product stream including a hydrogenation product, wherein the hydrogenation reactor system includes the liquid phase hydrogenation reactor and a liquid cooling loop, wherein the liquid cooling loop includes a pump having an inlet fluidly connected to an outlet of the liquid phase hydrogenation reactor, a heat exchanger having an inlet fluidly connected to an outlet of the pump and an outlet connected to an inlet of the liquid phase hydrogenation reactor; and during hydrogenating, injecting a flush liquid into the heat exchanger and against a solids accumulation on an inlet tube sheet of the heat exchanger.

In Aspect 2, the techniques described herein relate to the process of Aspect 1, wherein the solids accumulation includes a catalyst decomposition product.

In Aspect 3, the techniques described herein relate to the process of Aspect 1 or 2, further including: removing at least a portion of the solids accumulation from a header side of the inlet tube sheet.

In Aspect 4, the techniques described herein relate to any of Aspects 1 to 3, wherein injecting is performed intermittently.

In Aspect 5, the techniques described herein relate to the process of any of Aspects 1 to 4, wherein the flush liquid flows through at least one injection port located on the heat exchanger at a location that is upstream of the inlet tube sheet.

In Aspect 6, the techniques described herein relate to the process of Aspect 5, wherein an injection angle of the flush liquid relative to a plane of the inlet tube sheet is in a range of 0° to 90°.

In Aspect 7, the techniques described herein relate to the process of any of Aspects 5 to 6, wherein the at least one injection port includes at least two injection ports spaced equally along a circumference of the heat exchanger.

In Aspect 8, the techniques described herein relate to the process any of Aspects 5 to 7, further including: actuating a control valve to allow a flow of the flush liquid through the at least one injection port.

In Aspect 9, the techniques described herein relate to the process of any of Aspects 1 to 8, wherein an injection pressure of the flush liquid is greater than a pressure of a liquid reaction medium flowing through the heat exchanger.

In Aspect 10, the techniques described herein relate to the process of Aspect 9, wherein the injection pressure is provided by an injection pump fluidly coupled to the at least one injection port.

In Aspect 11, the techniques described herein relate to the process of any of Aspects 1 to 10, wherein the feed hydrocarbon is an aromatic hydrocarbon, wherein the hydrogenation product is a saturated hydrocarbon.

In Aspect 12, the techniques described herein relate to the process of Aspect 11, wherein the aromatic hydrocarbon is benzene, wherein the saturated hydrocarbon is cyclohexane.

In Aspect 13, the techniques described herein relate to the process of any of Aspect 1 to 12, wherein the flush liquid includes the hydrogenation product.

In Aspect 14, the techniques described herein relate to the process of any of Aspects 1 to 12, wherein the flush liquid consists of the hydrogenation product.

In Aspect 15, the techniques described herein relate to the process of any of Aspect 1 to 14, further including: introducing the feed hydrocarbon, hydrogen, and the homogeneous catalyst system into the liquid phase hydrogenation reactor; removing the gas phase product stream from the liquid phase hydrogenation reactor; removing a portion of a liquid reaction medium including a solid particulate from the liquid phase hydrogenation reactor; cooling the portion of the liquid reaction medium in the heat exchanger to form a cooled reaction medium; and introducing the cooled reaction medium to the liquid phase hydrogenation reactor.

In Aspect 16, the techniques described herein relate to the process of any of Aspects 1 to 15, wherein the hydrogenation reactor system further includes a gas phase reactor, the process further including: introducing the gas phase product stream to the gas phase reactor, wherein the gas phase product stream further includes unreacted feed hydrocarbon and unreacted hydrogen; hydrogenating the unreacted feed hydrocarbon with the unreacted hydrogen in a presence of a heterogeneous catalyst system in the gas phase reactor to form a reaction effluent stream; cooling the reaction effluent stream to form a cooled effluent stream including a liquid phase of the hydrogenation product and a gas phase of unreacted residual hydrogen; and separating the cooled effluent stream into a liquid stream including the hydrogenation product and a gas stream including the unreacted residual hydrogen.

In Aspect 17, the techniques described herein relate to the process of Aspect 16, wherein the flush liquid includes at least a portion of liquid stream.

In Aspect 18, the techniques described herein relate to a hydrogenation reactor system including: a liquid phase hydrogenation reactor containing a liquid reaction medium including a feed hydrocarbon, hydrogen, and a homogeneous catalyst system, wherein the liquid phase hydrogenation reactor is configured to hydrogenate the feed hydrocarbon with hydrogen in a presence of the homogeneous catalyst system to form a gas phase product stream including a hydrogenation product; and a liquid cooling loop connected to a liquid outlet of the liquid phase hydrogenation reactor and configured to cool a withdrawn portion of the liquid reaction medium, wherein the liquid cooling loop includes: a pump having an inlet fluidly coupled to a liquid outlet of the liquid phase hydrogenation reactor and configured to move the withdrawn portion of the liquid reaction medium through the liquid cooling loop; and a shell and tube heat exchanger including: an inlet header fluidly coupled to an outlet of the pump and an outlet header fluidly coupled to an inlet of the liquid phase hydrogenation reactor; an inlet tube sheet for a plurality of tubes, wherein the inlet tube sheet is fluidly coupled to the inlet header of the shell and tube heat exchanger; and an injection port placed on the inlet header of the shell and tube heat exchanger and configured to inject a flush liquid against a solids accumulation on the inlet tube sheet of the shell and tube heat exchanger.

In Aspect 19, the techniques described herein relate to the hydrogenation reactor system of Aspect 18, further including: an injection conduit connected to the injection port; and a control valve contained in the injection conduit and configured to actuate between an open position and a closed position so as to allow or disallow a flow of the flush liquid into the injection port.

In Aspect 20, the techniques described herein relate to the hydrogenation reactor system of Aspect 19, further including: a gas phase reactor configured to receive the gas phase product stream and to hydrogenate unreacted feed hydrocarbon with unreacted hydrogen received in the gas phase product stream to form a reaction effluent stream; a condenser configured to cool the reaction effluent stream to form a cooled effluent stream; and a separator configured to separate the cooled effluent stream into a gas stream and a liquid stream, wherein the injection conduit is fluidly coupled to the liquid stream.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A process comprising:
hydrogenating a feed hydrocarbon with hydrogen in liquid phase hydrogenation reactor of a hydrogenation reactor system in a presence of a homogeneous catalyst system to form a gas phase product stream comprising a hydrogenation product, wherein the hydrogenation reactor system comprises the liquid phase hydrogenation reactor and a liquid cooling loop, wherein the liquid cooling loop comprises a pump having an inlet fluidly connected to an outlet of the liquid phase hydrogenation reactor, a heat exchanger having an inlet fluidly connected to an outlet of the pump and an outlet connected to an inlet of the liquid phase hydrogenation reactor; and
during hydrogenating, injecting a flush liquid into the heat exchanger and against a solids accumulation on an inlet tube sheet of the heat exchanger.

2. The process of claim 1, wherein the solids accumulation comprises a catalyst decomposition product.

3. The process of claim 1, further comprising:
removing at least a portion of the solids accumulation from a header side of the inlet tube sheet.

4. The process of claim 1, wherein the flush liquid flows through at least one injection port located on the heat exchanger at a location that is upstream of the inlet tube sheet.

5. The process of claim 4, wherein an injection angle of the flush liquid relative to a plane of the inlet tube sheet is in a range of 0° to 90°.

6. The process of claim 4, wherein the at least one injection port comprises at least two injection ports spaced equally along a circumference of the heat exchanger.

7. The process of claim 4, wherein injecting is performed intermittently.

8. The process of claim 4, further comprising:
actuating a control valve to allow a flow of the flush liquid through the at least one injection port.

9. The process of claim 8, wherein an injection pressure of the flush liquid is greater than a pressure of a liquid reaction medium flowing through the heat exchanger.

10. The process of claim 9, wherein the injection pressure is provided by an injection pump fluidly coupled to the at least one injection port.

11. The process of claim 1, wherein the feed hydrocarbon is an aromatic hydrocarbon, wherein the hydrogenation product is a saturated hydrocarbon.

12. The process of claim 11, wherein the aromatic hydrocarbon is benzene, wherein the saturated hydrocarbon is cyclohexane.

13. The process of claim 1, wherein the flush liquid comprises the hydrogenation product.

14. The process of claim 1, wherein the flush liquid consists of the hydrogenation product.

15. The process of claim 1, further comprising:
introducing the feed hydrocarbon, hydrogen, and the homogeneous catalyst system into the liquid phase hydrogenation reactor;
removing the gas phase product stream from the liquid phase hydrogenation reactor;
removing a portion of a liquid reaction medium comprising a solid particulate from the liquid phase hydrogenation reactor;
cooling the portion of the liquid reaction medium in the heat exchanger to form a cooled reaction medium; and
introducing the cooled reaction medium to the liquid phase hydrogenation reactor.

16. The process of claim 1, wherein the hydrogenation reactor system further comprises a gas phase reactor, the process further comprising:
introducing the gas phase product stream to the gas phase reactor, wherein the gas phase product stream further comprises unreacted feed hydrocarbon and unreacted hydrogen;
hydrogenating the unreacted feed hydrocarbon with the unreacted hydrogen in a presence of a heterogeneous catalyst system in the gas phase reactor to form a reaction effluent stream;
cooling the reaction effluent stream to form a cooled effluent stream comprising a liquid phase of the hydrogenation product and a gas phase of unreacted residual hydrogen; and
separating the cooled effluent stream into a liquid stream comprising the hydrogenation product and a gas stream comprising the unreacted residual hydrogen.

17. The process of claim 16, wherein the flush liquid comprises at least a portion of liquid stream.

18. A hydrogenation reactor system comprising:
a liquid phase hydrogenation reactor containing a liquid reaction medium comprising a feed hydrocarbon, hydrogen, and a homogeneous catalyst system, wherein the liquid phase hydrogenation reactor is configured to hydrogenate the feed hydrocarbon with hydrogen in a presence of the homogeneous catalyst system to form a gas phase product stream comprising a hydrogenation product; and
a liquid cooling loop connected to a liquid outlet of the liquid phase hydrogenation reactor and configured to cool a withdrawn portion of the liquid reaction medium, wherein the liquid cooling loop comprises:
a pump having an inlet fluidly coupled to a liquid outlet of the liquid phase hydrogenation reactor and configured to move the withdrawn portion of the liquid reaction medium through the liquid cooling loop; and
a shell and tube heat exchanger comprising:
an inlet header fluidly coupled to an outlet of the pump and an outlet header fluidly coupled to an inlet of the liquid phase hydrogenation reactor;
an inlet tube sheet for a plurality of tubes, wherein the inlet tube sheet is fluidly coupled to the inlet header of the shell and tube heat exchanger; and
an injection port placed on the inlet header of the shell and tube heat exchanger and configured to inject a flush liquid against a solids accumulation on the inlet tube sheet of the shell and tube heat exchanger.

19. The hydrogenation reactor system of claim 18, further comprising:
an injection conduit connected to the injection port; and
a control valve contained in the injection conduit and configured to actuate between an open position and a closed position so as to allow or disallow a flow of the flush liquid into the injection port.

20. The hydrogenation reactor system of claim 19, further comprising:
a gas phase reactor configured to receive the gas phase product stream and to hydrogenate unreacted feed hydrocarbon with unreacted hydrogen received in the gas phase product stream to form a reaction effluent stream;
a condenser configured to cool the reaction effluent stream to form a cooled effluent stream; and
a separator configured to separate the cooled effluent stream into a gas stream and a liquid stream,
wherein the injection conduit is fluidly coupled to the liquid stream.

* * * * *